United States Patent
Andersen et al.

(10) Patent No.: US 11,628,443 B2
(45) Date of Patent: Apr. 18, 2023

(54) DEVICE AND A METHOD FOR TESTING A BIOLOGICAL SAMPLE, PREFERABLY SEMEN

(71) Applicant: EXSEED HEALTH APS, Copenhagen S (DK)

(72) Inventors: Emil Andersen, Copenhagen V (DK); Morten Gorm Ulsted, London (GB); Daniel Gewecke Daugaard-Jensen, Copenhagen SV (DK); Carsten Petersen, Højbjerg (DK)

(73) Assignee: EXSEED HEALTH APS

( * ) Notice: Subject to any disclaimer, the term of this patent is extended or adjusted under 35 U.S.C. 154(b) by 424 days.

(21) Appl. No.: 16/645,361

(22) PCT Filed: Sep. 7, 2018

(86) PCT No.: PCT/DK2018/050224
§ 371 (c)(1),
(2) Date: Mar. 6, 2020

(87) PCT Pub. No.: WO2019/048018
PCT Pub. Date: Mar. 14, 2019

(65) Prior Publication Data
US 2020/0282402 A1     Sep. 10, 2020

(30) Foreign Application Priority Data

Sep. 8, 2017   (DK) .......................... PA 2017 70672

(51) Int. Cl.
*B01L 9/00*       (2006.01)
*G06T 7/70*       (2017.01)
(Continued)

(52) U.S. Cl.
CPC ............... *B01L 9/52* (2013.01); *G01N 15/06* (2013.01); *G01N 33/487* (2013.01);
(Continued)

(58) Field of Classification Search
None
See application file for complete search history.

(56) References Cited

U.S. PATENT DOCUMENTS 9,057,702 B2   6/2015   Ozcan et al.
9,959,621 B2   5/2018   Hsu et al.
(Continued)

FOREIGN PATENT DOCUMENTS

CN        107144568 A     6/2017
EP         2781910 A1     9/2014
(Continued)

OTHER PUBLICATIONS

Kanakasabapathy, et al., "An automated smartphone-based diagnostic assay for point-of-care semen analysis", Science Translational Medicine, 2017, vol. 9, issue 382.
(Continued)

*Primary Examiner* — James M Anderson, II
(74) *Attorney, Agent, or Firm* — Kim IP Law Group LLC

(57) ABSTRACT

A device for testing the quality of a biological sample, preferably semen, in cooperation with an electronic apparatus, the device comprising; a slide slot adapted for receiving a slide containing a biological sample; a receiving surface adapted for receiving an electronic apparatus containing a camera, where the receiving surface comprises a through hole extending through said receiving surface; a light source arranged opposite the through hole; a lens arranged between the slide slot and the receiving surface, and adapted to magnify the image received at the receiving surface; where the slide slot is arranged between the light source and the through hole, the device further comprising a housing attached opposite the receiving surface, the housing having a shape allowing for a plurality of stable resting conditions in which the electronic apparatus lies on the receiving surface, and alignment between the camera and the through hole is maintained by friction.

15 Claims, 8 Drawing Sheets

(51) Int. Cl.
  *G01N 15/06* (2006.01)
  *G01N 33/487* (2006.01)
  *G06T 7/00* (2017.01)
  *H04N 23/54* (2023.01)
  *H04N 23/55* (2023.01)
  *H04N 23/56* (2023.01)
  *G01N 15/00* (2006.01)

(52) U.S. Cl.
  CPC .............. *G06T 7/0012* (2013.01); *G06T 7/70* (2017.01); *H04N 23/54* (2023.01); *H04N 23/55* (2023.01); *H04N 23/56* (2023.01); *B01L 2300/0654* (2013.01); *G01N 2015/0065* (2013.01); *G01N 2015/0693* (2013.01); *G06T 2207/10016* (2013.01); *G06T 2207/30024* (2013.01)

(56) References Cited

U.S. PATENT DOCUMENTS

| | | | | |
|---|---|---|---|---|
| 2013/0273528 | A1* | 10/2013 | Ehrenkranz | G01N 33/558 435/7.9 |
| 2014/0213468 | A1* | 7/2014 | Ehrenkranz | G01N 33/558 436/500 |
| 2014/0254004 | A1 | 9/2014 | Wooder et al. | |
| 2015/0185159 | A1 | 7/2015 | Morita et al. | |
| 2015/0304555 | A1 | 10/2015 | Ehrenkranz | |
| 2016/0062099 | A1 | 3/2016 | Shankar et al. | |
| 2018/0181792 | A1* | 6/2018 | Shafiee | H04N 5/2256 |

FOREIGN PATENT DOCUMENTS

| | | |
|---|---|---|
| EP | 2839280 B1 | 12/2016 |
| EP | 3244250 A1 | 11/2017 |
| WO | 99/42557 A1 | 2/1999 |
| WO | 2012088351 A2 | 6/2012 |
| WO | 2014021928 A2 | 2/2014 |
| WO | 2015087232 A1 | 6/2015 |
| WO | 2015164322 A1 | 10/2015 |
| WO | 2016209943 A1 | 12/2016 |
| WO | 17197072 A1 | 11/2017 |

OTHER PUBLICATIONS

International Search Report dated Nov. 14, 2018 in International Application No. PCT/DK2018/050224.
International Preliminary Report on Patentability dated Dec. 20, 2019 in International Application No. PCT/DK2018/050224.

* cited by examiner

DEVICE AND A METHOD FOR TESTING A BIOLOGICAL SAMPLE, PREFERABLY SEMEN

CROSS-REFERENCE TO RELATED APPLICATIONS

This application is a U.S. national phase application under 35 U.S.C. § 371 of International Patent Application No. PCT/DK2018/050224 filed Sep. 7, 2018, which claims priority to Denmark Patent Application No. PA 2017 70672 filed Sep. 8, 2017, the entire disclosures of which are hereby incorporated by reference in their entirety.

Technical Field

The present invention relates to a device for testing a biological sample, preferably semen. The invention further relates to a method for testing a biological sample. The invention also relates to a use of an electronic apparatus, arranged on a receiving surface of a device, for improving sperm quality.

BACKGROUND ART

Testing the quality of semen is associated with many issues; the sample of semen must be extracted or deposited outside of the user's home, which may be considered inconvenient, uncomfortable, or embarrassing. Depositing the sample of semen with a testing facility may cause the result to be delayed. Furthermore, depositing the sample introduces a chance of contamination or mix up of samples.

By enabling the user to perform such tests at home, many of the practical and psychological issues are resolved. Furthermore, these tests can be performed more often, as the cost of performing the tests is low, both in terms of resources and time. By performing the test more frequently, trends in the semen quality can be monitored and benefits of positive lifestyle changes may be observed and enhanced.

WO16209943 describes a system containing an optical assembly with a lens and a microfluidic chip containing a semen sample where the semen sample is aligned to the optical assembly. The optical assembly may be in a housing, which engages with an electronic apparatus containing a camera for aligning the camera with the optical axis of the optical assembly.

SUMMARY

According to a first aspect, the invention relates to a device for testing the quality of a biological sample, preferably semen, in cooperation with an electronic apparatus, where the device comprises;

a slide slot adapted for receiving a slide containing a biological sample;

a receiving surface adapted for receiving an electronic apparatus containing a camera, where the receiving surface comprises a through hole extending through said receiving surface, so that when the electronic apparatus is placed on said receiving surface, the through hole is arranged adjacent to the camera of the electronic apparatus;

a light source arranged opposite the through hole, and adapted to emit light that illuminates and at least partly propagates through the sample and said through hole, such that a camera, when placed at the through hole, receives at least part of the emitted light;

a lens arranged between the slide slot and the receiving surface, and adapted to magnify the image received at the receiving surface;

where the slide slot is arranged between the light source and the through hole.

Consequently, by having a receiving surface the electronic apparatus may easily and conveniently be placed on the device, where the camera of the electronic apparatus is placed adjacent to the through hole.

By the slide slot being adapted for receiving a slide it is understood to constitute that the slot has dimensions which accommodate the slide and that the slide slot comprises fixation means, which allow the slide to be fixated.

By the receiving surface being adapted for receiving an electronic apparatus it is understood that the electronic apparatus can be placed adjacent or in abutment without any obstruction from the receiving surface.

By the through hole extending through the surface it is understood that the through hole provides optical access to the slide slot for the electronic apparatus when adjacent to the receiving surface.

By the camera of the electronic apparatus being placed adjacent to the through hole it is understood that the camera is substantially aligned to the optical axis of the through hole, whereby the field of view of the camera through the through hole is not blocked by the device, and at least part of the slide slot is visible for the camera.

By illuminating the sample, an illuminated image of the biological sample is created, which can be detected by the camera of the electronic apparatus. By partly propagating through said through hole to the camera it is understood that part of the light may be lost due to absorption or scattering. Furthermore, part of the light may be lost if the illuminated area of the sample is larger than the dimensions of the through hole, or if the illuminated image is not aligned to the through hole, causing an obstruction of the illuminated image by the through hole.

By arranging the lens between the slide and the camera it is understood that the image generated by the illumination of the slide propagates through the lens before reaching the camera.

By magnifying the image, it is understood that the image of the sample reaching the camera is increased in dimensions compared to the image generated at the sample.

The device may be made substantially from plastic, in particular the structural parts of the device may be 3D printed, thermoformed injection moulded, or pressed.

The slide slot may be adapted to receive the slide by having inner dimensions substantially matching the outer dimension of the slide. The slide slot may have a repositioning means adapted to reposition the slide with respect to the through hole. The slide slot may be provided with a clip, which secures the slide. The slide slot may be provided with a spring loaded release mechanism for releasing the slide. The slide may preferably be a glass slide.

The receiving surface may be made from or coated with a high friction material assisting in maintaining the alignment between the through hole and the camera of the electronic apparatus.

The through hole may be constructed as a cylinder or a cuboid. The through hole may have an open face in a first end, a second end, or both. The through hole may have a transparent covering face in a first end, a second end, or both. The covering face may be scratch resistant. The through hole may be provided with a removable and re-attachable covering cap at a first end.

The light source may be a LED-light, a light bulb or a reflector reflecting a natural light source or an electrical light source onto the sample. The light source may be powered by an internal power source, an external power source or the electronic apparatus. The light source may have a spectrum in the visible light spectrum, ultraviolet spectrum or the infrared spectrum. The light source may comprise optical components collimating the light source, focusing the light source onto the sample or defocusing the light source onto the sample. The optical components may be movable and/or replaceable.

The lens may be a ball lens, concave lens, convex lens, an aspheric lens, a plano-convex lens, a convexo-concave lens, a GRIN lens, or a lens assembly. The magnification of the lens may be larger than 50 times, preferably larger than 100 times, most preferably larger than 150 times. The lens may be movable using piezoelectric motors, voice coil magnetic drivers or mechanical displacement.

In some embodiments the device further comprises a housing attached to the device opposite the receiving surface, the housing having an inner side and an outer side opposite the inner side;

where the inner side is oriented towards the receiving surface and the outer side is oriented away from the receiving surface, such that the slide slot is arranged closer to the inner side than the outer side;

where the outer side has at least two faces, the two faces are arranged at an angle to each other, where the device is stable, when the device is arranged on either face, so that alignment of the through hole with a camera of an electronic apparatus is retained, when an electronic apparatus is placed on the receiving surface. The angle may be equal to or less than 90°, 80°, 70°, 60°, 50°, 45°, 40°, 30°, 20°, or 10°. The at least two faces may form a rounded shape of the outer side. The housing may have a semi-circular shape allowing a plurality of stable resting conditions.

In some embodiments, the device further comprises a housing attached opposite the receiving surface, the housing having a shape allowing for a plurality of stable resting conditions in which the electronic apparatus lies on the receiving surface, and alignment between the camera and the through hole is maintained by friction.

In some embodiments, the device further comprises a housing attached opposite the receiving surface, wherein an outer side of the housing has a shape configured to support the device in a plurality of stable resting conditions, where the device is stable, when the device is arranged in a plurality of stable resting conditions, so that alignment of the through hole with a camera of an electronic apparatus is retained, when an electronic apparatus is placed on the receiving surface.

A stable resting condition may be characterized as a condition where the electronic apparatus lies on the receiving surface, and alignment between the camera and the through hole is maintained by friction without the influence of the user.

A stable resting condition may alternatively be characterized as a condition where the device is supported by a substantially planar surface and the electronic apparatus is supported on the receiving surface and the substantially planar surface, and alignment between the camera and the through hole is maintained by friction.

Consequently, the device can be used with electronic apparatuses with different geometries without modifying the device.

The housing may encompass the slide slot, the light source, and/or the lens. The entrance of the slide slot enables the insertion of a slide in the slide slot from the exterior.

The outer side may be provided with a plurality of faces, where the device may be arranged on any of the faces. Preferably, the outer side may be provided with a plurality of faces arranged as a half circle.

The housing may be made from the same material as the device. The housing may be detachable, allowing for replacement of light source, lens, and/or other internal mechanism.

In some embodiments, the outer side of the housing has a large coefficient of friction.

Consequently, the device does not slide when placed on a surface, whereby retention of the alignment between a camera and a through hole is facilitated.

The coefficient of friction may be larger than 0.3, preferably larger than 0.5, most preferably larger than 0.7.

In some embodiments the receiving surface and the housing are separate elements.

Consequently, the production of the device is simplified.

The receiving surface and the housing may be provided assembled or disassembled.

In some embodiments the lens is arranged in the through hole.

Consequently, the lens is aligned to the optical axis of the through hole, providing an optimal image.

By arranged in the through hole it is understood that the lens does not protrude through openings in either a first end or a second end of the through hole.

In some embodiments the slide slot extends partially along the receiving surface.

Consequently, the electronic apparatus, when adjacent to the receiving surface, and the slide, when inserted, are arranged laterally.

In a second aspect, the present invention relates to a method for testing the quality of a biological sample, preferably semen, comprising the steps of:

recording a video of the biological sample with a camera of an electronic apparatus;

identifying a plurality of biological cells in the biological sample based on the recorded video;

determining a location of a first biological cell of the plurality of biological cells in a first frame of the recorded video;

identifying the first biological cell in a second frame of the recorded video;

determining a location of the first biological cell in the second frame;

returning the detected motility and/or concentration of the plurality of biological cells in the biological sample.

Consequently, the cost associated with performing an analysis of the sample is reduced.

By identifying a plurality of biological cells, it is understood that cells are distinguished from the surroundings.

By measuring the motility of the detected cells, it is understood that the detected cells are divided into two categories of cells that are moving and not moving, by taking the ratio of the moving cells to the total number of cells the motility is deduced. Velocity and movement pattern may be used to determine normal motility. By measuring the concentration, it is understood that from the number of detected cells within a certain area and with knowledge of the thickness of the sample reservoir, the average number of cells per volume can be inferred.

By returning the detected motility and/or concentration of the plurality of biological cells in the biological sample, it is understood that the measured values are stored and/or presented on a screen on the electronic apparatus.

The electronic apparatus may be a smartphone, tablet, or computer. The video may be recorded in the standard video recording application of the electronic apparatus. Alternatively, the video may be recorded in an application, which also performs the analysis.

The biological cells in the recorded video may be detected using phase contrasts or stainings. The biological cells may be detected using their shape or their movement.

In some embodiments, the method further comprises the step of providing a device according to the first aspect of the invention. The method may comprise the step of placing the electronic apparatus on the receiving surface of the device.

In some embodiments, the method further comprises the step of uploading the video, the detected motility, concentration of the biological sample, or any combination to an external apparatus.

Consequently, further analysing capacity is available. Furthermore, the recorded video and data can be backed-up and shared among the user's apparatuses.

The step of uploading the recorded video and/or the measured motility and concentration of the detected biological cells to an external device may occur at any step after the video has been recorded. The identification of biological cells may occur on either the electronic apparatus or the external apparatus.

The measured values may be stored on the external apparatus.

The external apparatus may be a server or a personal computer.

In some embodiments, the method further comprises providing a digital label to the detected cell concentration.

Consequently, a simple characterization scheme is obtained, which may be used to guide decision making in the process of conceiving. Furthermore, by labelling samples with low concentration for additional analysis, erroneous labelling due to user error can be avoided or users with critically low concentration can be referred to experts.

The digital labelling of the measured cell concentration may be provided as a classification system, where a cell concentration higher than 50M/ml is labelled high, a cell concentration between 15-55M/ml is labelled moderate, a cell concentration between 5-15M/ml is labelled low, and a cell concentration between 0-5M/ml labels the sample for additional analysis.

The additional analysis may comprise of recording a secondary video and performing a secondary analysis. The additional analysis may be performed by a software application. Alternatively, the additional analysis may be performed by a human operator.

In some embodiments, the method further comprises the step of placing an electronic apparatus on the receiving surface of a device according to the first aspect of the invention, such that the camera of the electronic apparatus is arranged adjacent to the through hole of the device, the step preferably being performed before the step of recording a video of the biological sample with an electronic apparatus.

Consequently, the device provides a stable, illuminated, and magnified image of the biological sample for the electronic apparatus to record.

In a third aspect, the present invention relates to use of an electronic apparatus, arranged on the receiving surface of a device according to the first aspect of the invention, for improving sperm quality, comprising:

inputting first information regarding physical health into the electronic apparatus;

inputting second information regarding lifestyle into the electronic apparatus;

deriving lifestyle recommendations for improving the sperm quality based on the first and second information;

returning the lifestyle recommendations.

Consequently, the user can implement and test lifestyle recommendations.

The first information may comprise the user's age, body mass index, blood pressure, blood sugar level, cholesterol level, testosterone level and/or estradiol level. The first information may comprise the user's general medical condition or general medication intake. The first information may comprise a result of a testicular examination, and/or the urological conditions of the user. The first information may comprise information about frequency of intercourse and/or the period for which the user has been trying to conceive.

The second information may comprise the exercise level of the user, which may consist of the number of daily steps, the amount of aerobic exercise, the amount of resistance exercise, and/or general daily living.

The second information may comprise information about the user's diet, which may consist information about consumption of fast food, fried food, vegetables, fruits, nuts, alcohol, and supplements.

The second information may comprise information about the psychological state of the user, which may comprise information about the user's sleep duration and quality, energy level, stress level, and/or general emotional health.

The second information may comprise information about toxins and testicle care of the user, which may comprise information about the user's use of tight pants or frequent sitting, smoking, exposure to heat, exposure to cell phone in groin area, use of sunscreen, and/or use of lotion, soap, and perfume.

The lifestyle recommendations may be derived through an algorithm, which, based on the sperm analysis and first and second information, assigns numerical value to lifestyle changes. The lifestyle recommendation may be ranked based on numerical values assigned by an algorithm.

In some embodiments, the use further comprises the step of:

inputting third information regarding the current sperm quality into the electronic apparatus, the third information comprises at least the sperm concentration and motility;

deriving lifestyle recommendations for improving the sperm quality based on the first, second and third information.

Consequently, the current sperm quality is taken into account when deriving the lifestyle recommendations. Furthermore, the sperm quality can be tracked over time, whereby beneficial lifestyle changes can be identified and continued and, conversely, harmful lifestyle changes can be ceased.

The inputting of third information may occur before or after the first and/or second information has been inputted.

In some embodiments, the third information is obtained through a method according to the second aspect of the invention.

Consequently, the third information may be obtained by a user at home without the assistance of an outside facility.

The different aspects of the present invention can be implemented in different way including a device for testing a biological sample, a method for testing a biological sample, a use of an electronic apparatus, arranged on a receiving surface of a device, for improving sperm quality, described above and in the following, each yielding one or more of the benefits and advantages described in connection with at least one of the aspects described above, and each having one or more preferred embodiments corresponding to the preferred embodiments described in connection with at least one of the aspects described above and/or disclosed in dependent claims. Furthermore, it will be appreciated that embodiments described in connection with one of the aspects described herein may equally be applied to the other aspects.

BRIEF DESCRIPTION OF THE DRAWINGS

FIG. 1 shows a perspective view, FIG. 2 shows a top view, FIG. 3 shows a side view, FIG. 4 shows a side view through a cut through plane, and FIG. 5 shows an end view.

DETAILED DESCRIPTION OF EMBODIMENTS

Figure 1:
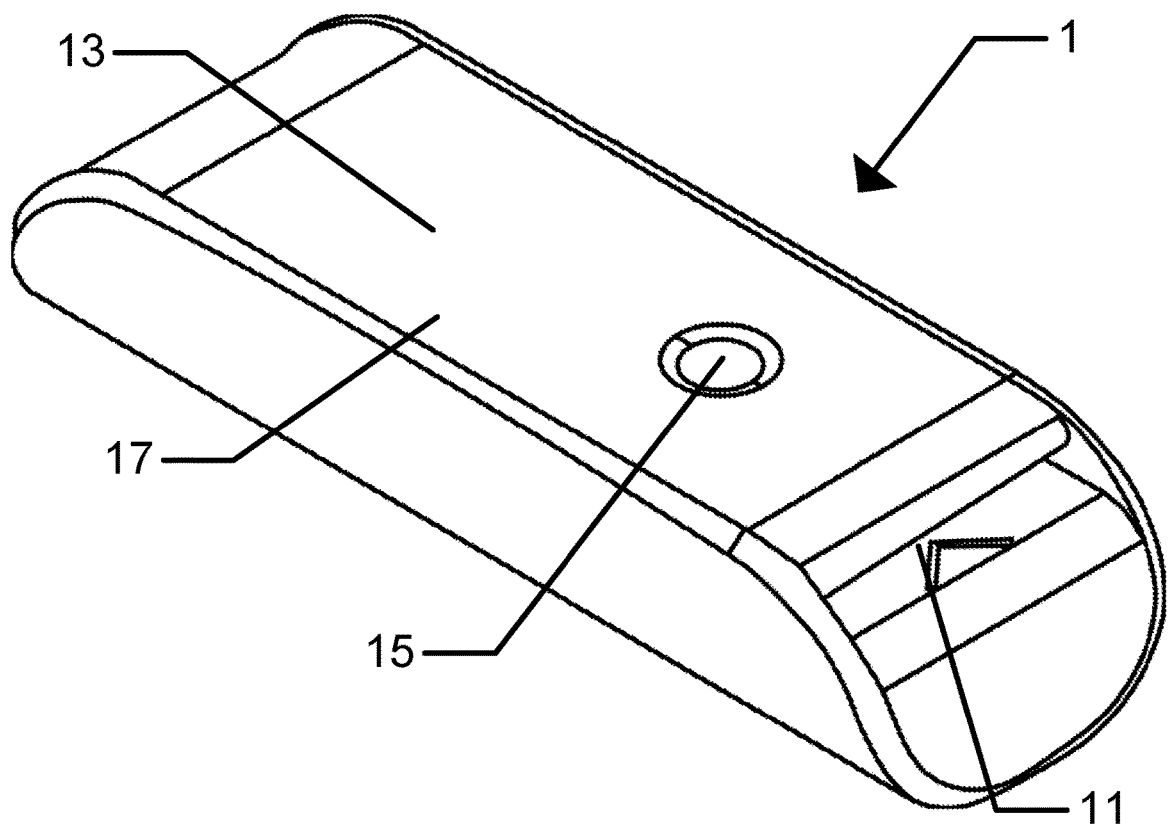
FIGS. 1 to 5 show a device for testing a biological sample according to an embodiment of the invention.
Figure 2:
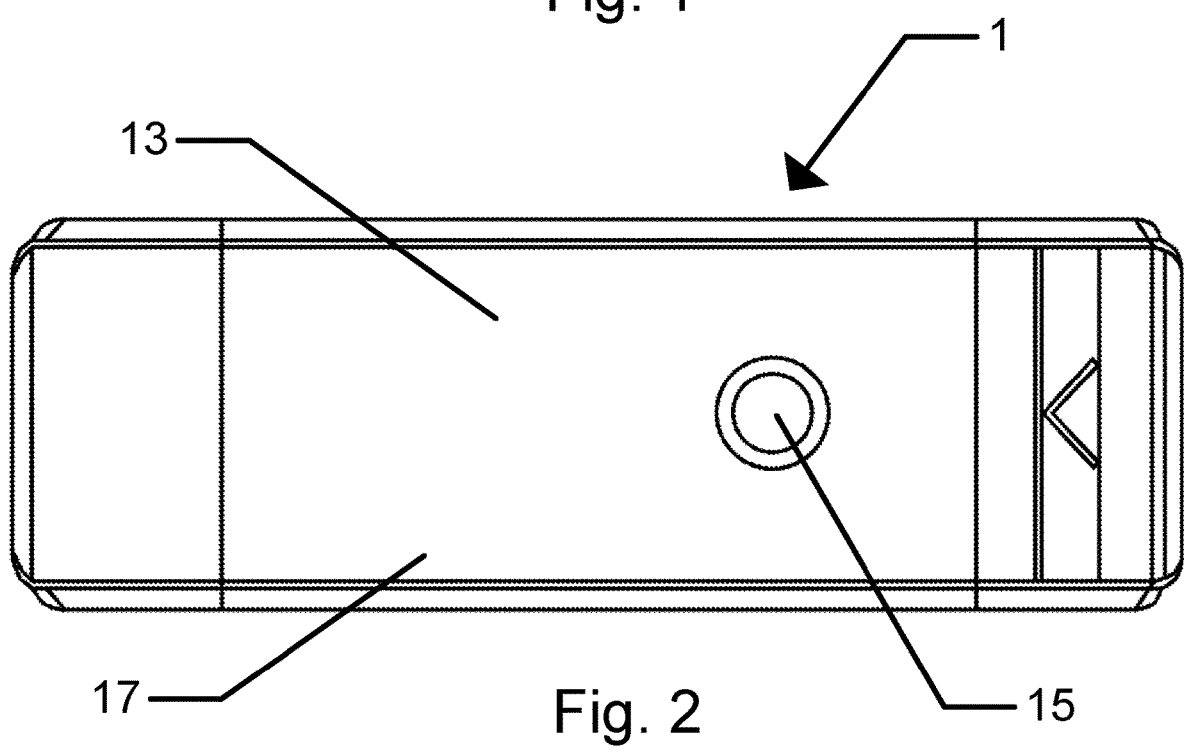
Figure 3:
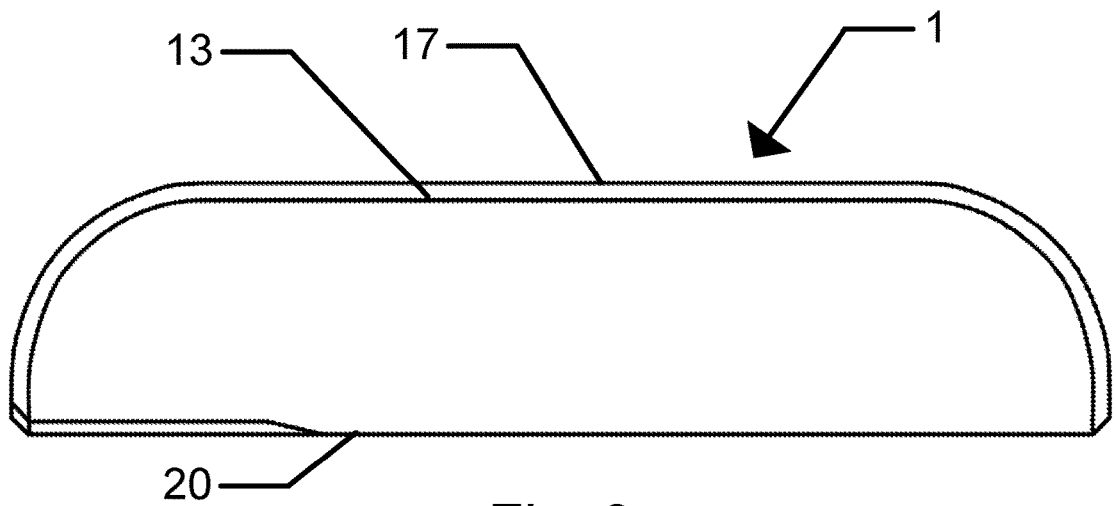
Figure 4:
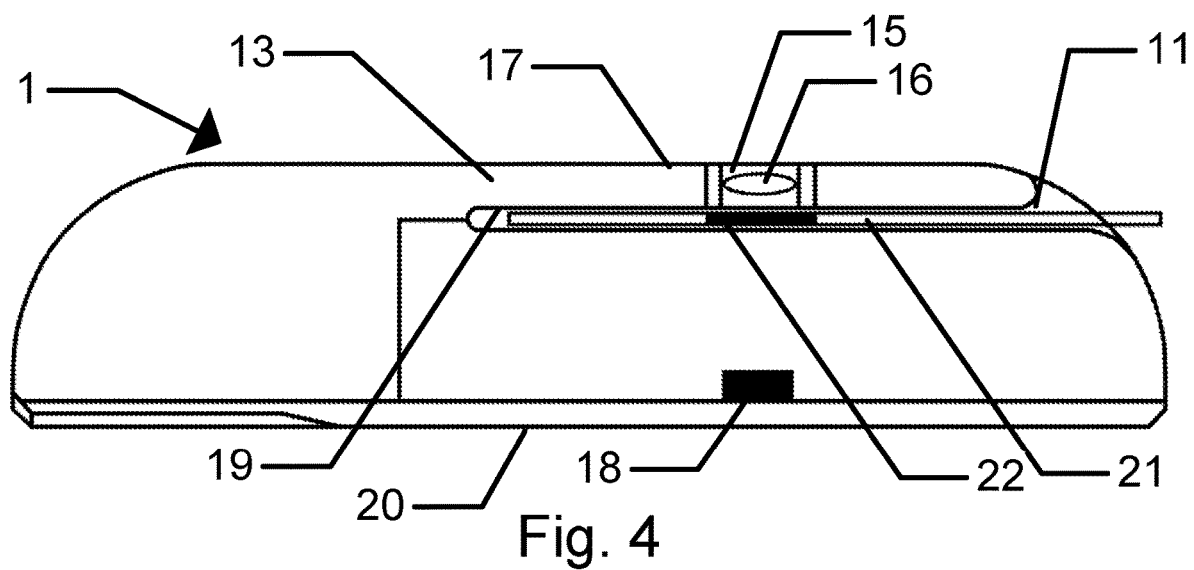
Figure 5:
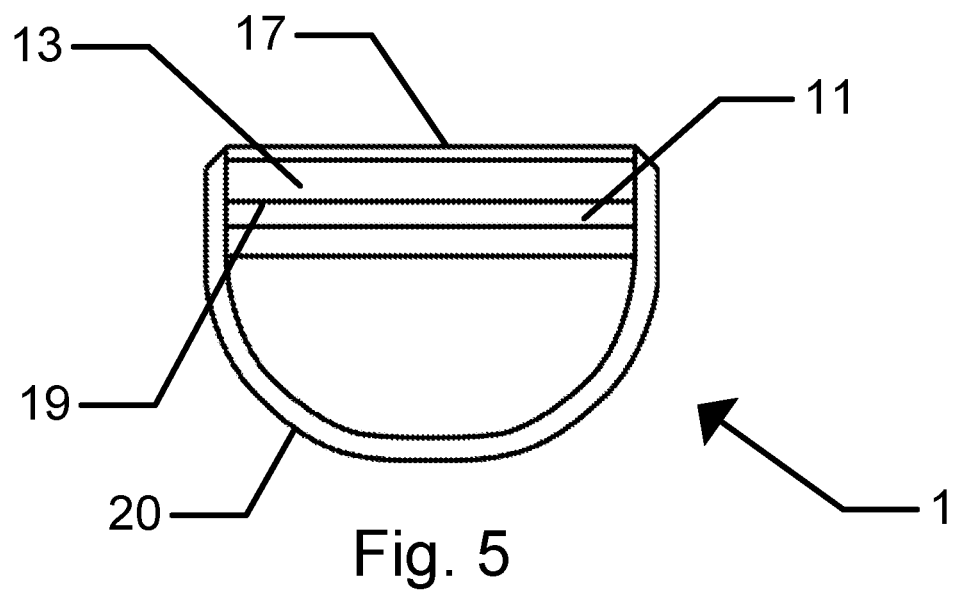

In the following description, reference is made to the accompanying figures, which show by way of illustration how the invention may be practiced.

FIGS. 1 to 5 show a device 1 for testing a biological sample according to an embodiment of the invention. The device 1 has a slide slot 11 adapted for receiving a slide 21 preferably a biological sample 22, a receiving surface 13 adapted for receiving an electronic apparatus (not shown) containing a camera. The receiving surface 13 comprises a through hole 15 extending through said surface 13, so that when the electronic apparatus is arranged on said receiving surface 13, the through hole 15 is adjacent to the camera of the electronic apparatus. The device 1 further has a light source 18 arranged opposite the through hole 15, so that when the light source 18 is activated, the electronic apparatus is arranged on said receiving surface 13 and a slide 21 with a biological sample 22 is arranged in the slot 11, the light will illuminate the biological sample 22 and partly propagate through said through hole 15 to the camera. The device 1 also comprises a lens 16 arranged between the slide slot 11 and the camera of the electronic apparatus, so that the image is magnified before reaching the camera, where the slide slot 11 is arranged between the light source 18 and the through hole 15. The through hole 15 extends from a first side 17 of the receiving surface to a second side 19 of the receiving surface 13.

The device 1 further comprises a housing 20 attached to the device 1 opposite the receiving surface 13, so that the housing 20 surrounds the slide slot 11, light source 18 and lens 16, and the housing 20 is provided with an entrance 19 to the slide slot 11, wherein the housing 20 has a shape allowing for a plurality of stable resting conditions. In the embodiment shown in FIGS. 1 to 5, these stable resting conditions are provided by way of a rounded, specifically a semi-circular, shape, however other shapes may be envisioned.

Figure 6A:
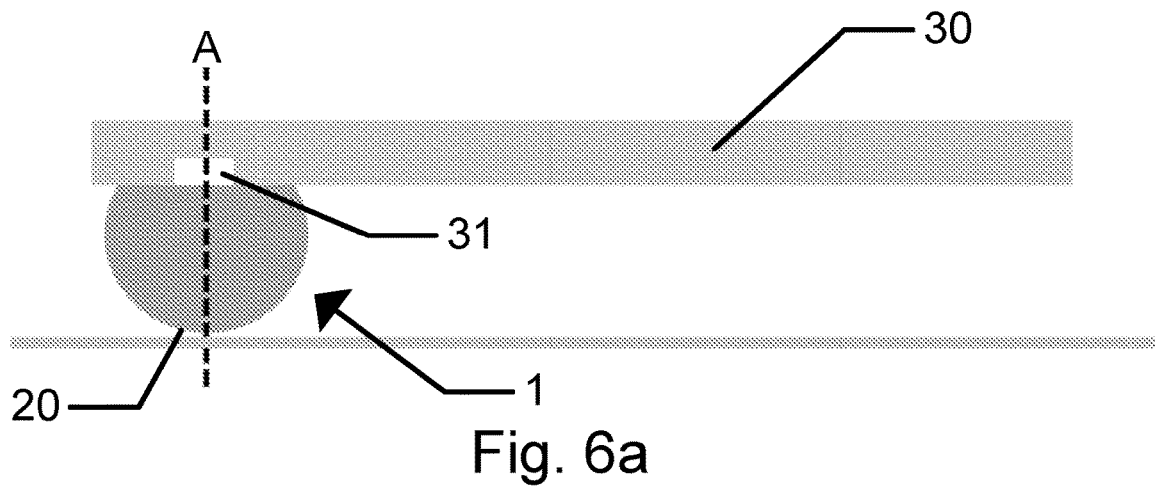
FIG. 6a-c shows an electronic apparatus having a camera on a device for testing a biological sample according to an embodiment of the invention.
Figure 6B:
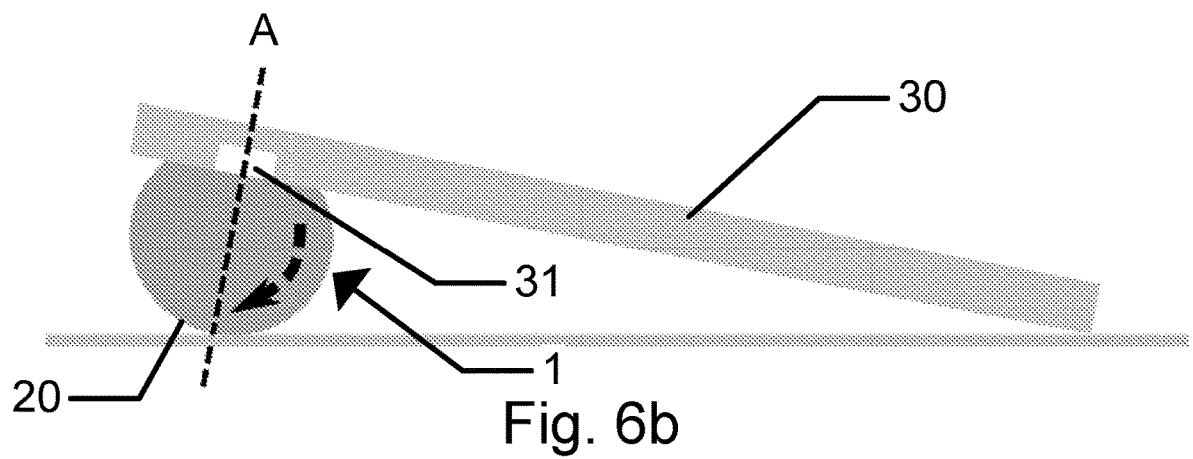
Figure 6C:
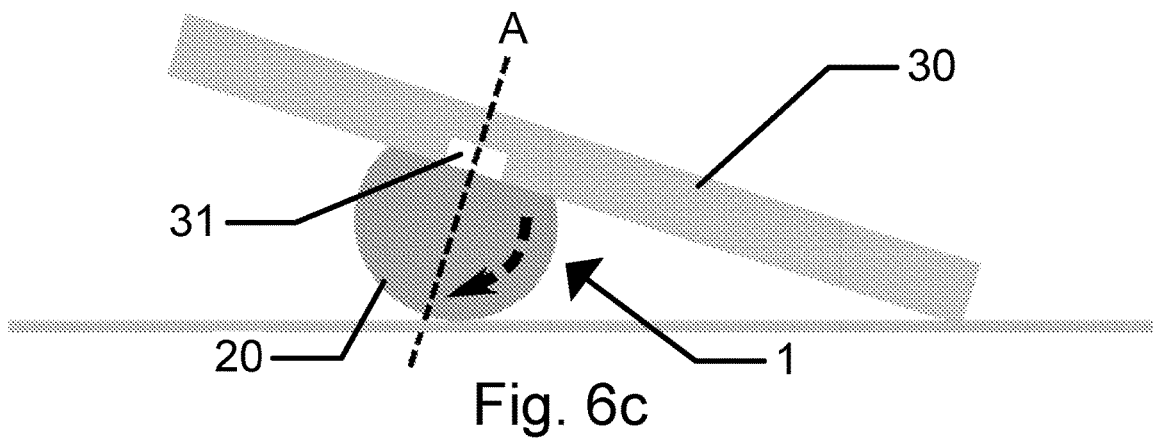

FIGS. 6a to 6c illustrate how the housing 20 of the device 1 allows for a plurality of stable resting conditions, in which the device 1 and the electronic apparatus are supported on a substantially planar surface, whereby electronic apparatuses 30 of different geometry can be utilized with the same device 1. In FIG. 6a an electronic apparatus 30 containing a camera 31 is placed on the device 1 such that the camera 31 is aligned with an axis A. The axis A is aligned to the lens, through hole, and light source of the device 1. In FIG. 6a the electronic apparatus 30 is not in a stable resting condition because the electronic apparatus 30 is only shown supported on the device and not fully supported by the substantially planar surface. FIG. 6b shows the electronic apparatus 30 in a stable resting condition, in which the electronic apparatus 30 is supported on the receiving surface 13 of the device 1 and an edge of the electronic apparatus 30 is supported on the substantially planar surface, which also supports the device 1. In order to maintain the alignment of the camera 31 with the axis A, the device 1 has been rotated. FIG. 6c shows an electronic apparatus 30, where the camera 31 is oriented closer to the central axis of the electronic apparatus 30. In order to accommodate such an electronic apparatus 30, while maintaining the alignment between the camera 31 and the axis A, the electronic apparatus 30 is moved and the device 1 is rotated.

Figure 7:
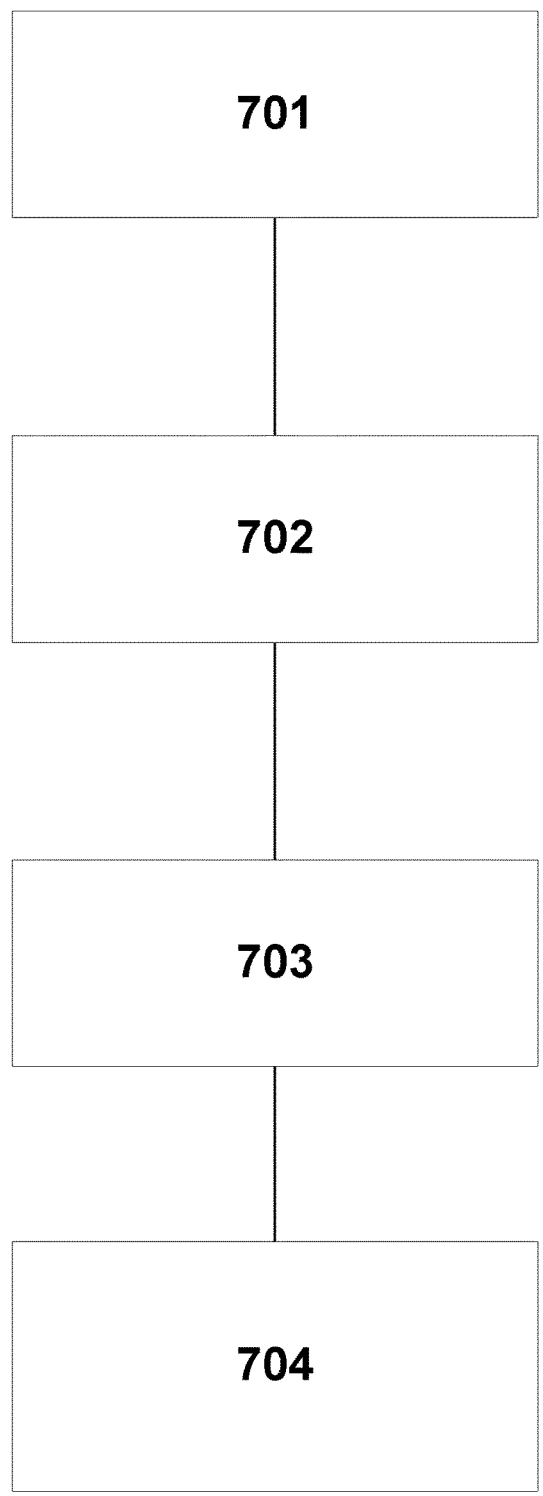
FIG. 7 shows an example of a method for testing a biological sample according to an embodiment of the invention.

FIG. 7 shows an embodiment of the method for determining the quality of a biological sample. In 701, a video of the sample is recorded. In 702 software automatically detect cells in the biological sample. In 703 the motility and the concentration of the detected cells are measured. In 704 the measured motility and concentration is returned.

Figure 8:
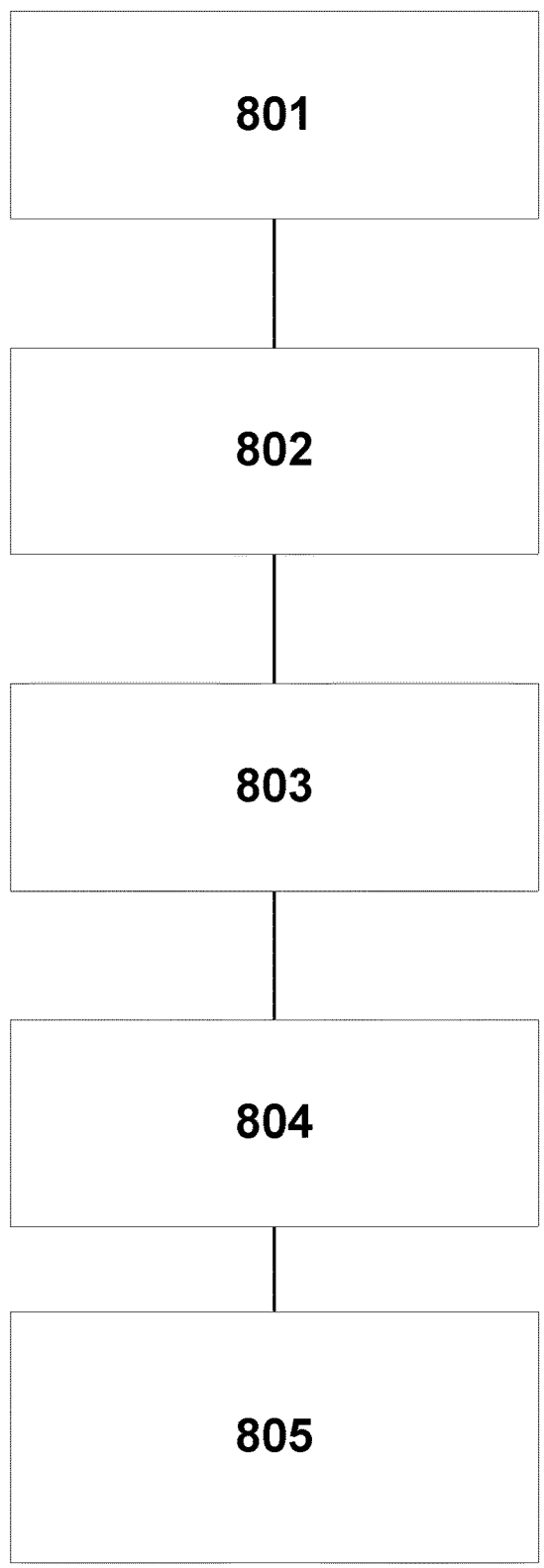
FIG. 8 shows an example of a method for testing a biological sample according to an embodiment of the invention.

FIG. 8 shows an embodiment of the method for determining the quality of a biological sample. In 801, a video of the sample is recorded. In 802 the recorded video is uploaded to an internet connected device. In 803 software automatically detect cells in the biological sample. In 804 the motility and the concentration of the detected cells are measured. In 805 the measured motility and concentration is returned.

Figure 9:
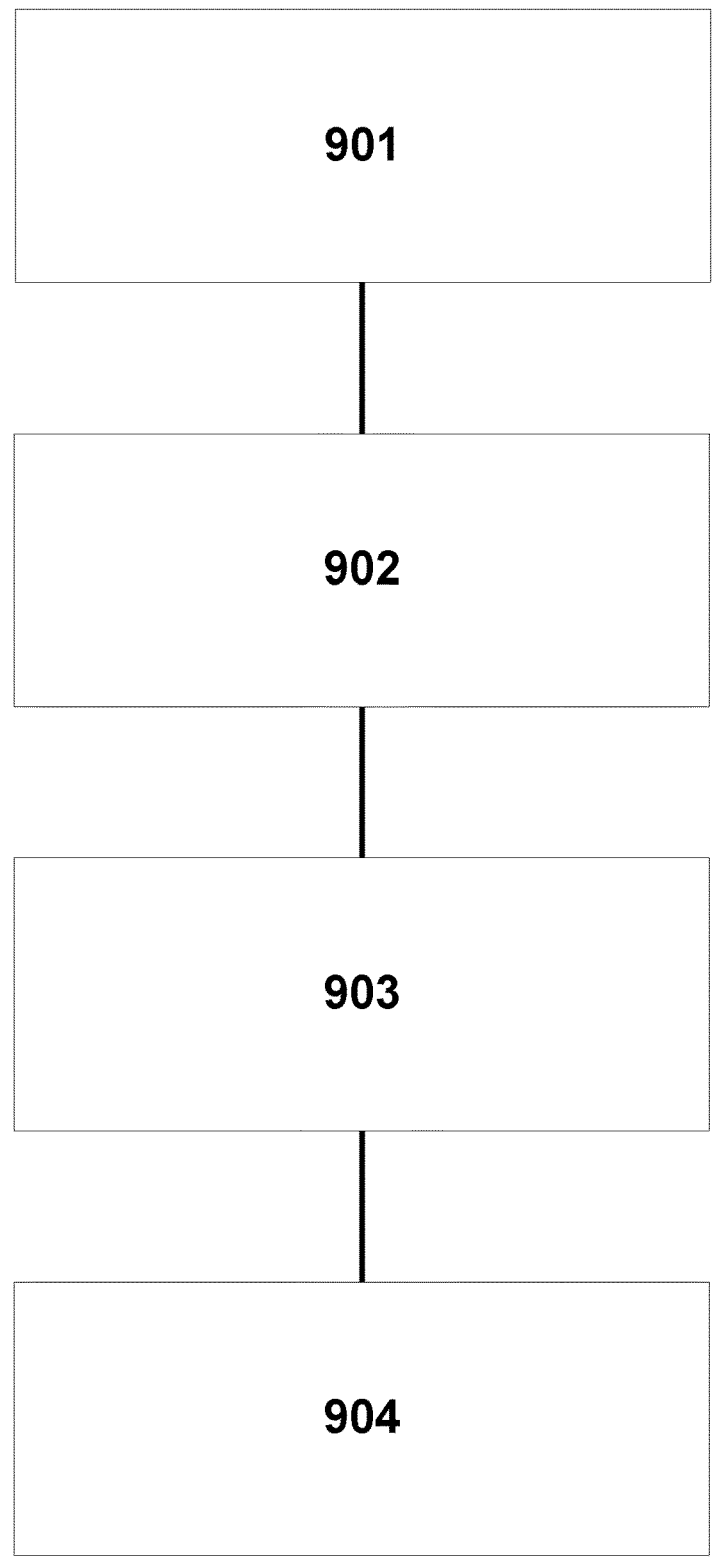
FIG. 9 shows an example of use of an electronic apparatus, arranged on the receiving surface of a device for improving the sperm quality according to an embodiment of the invention.

FIG. 9 shows an embodiment of the use of an electronic apparatus, arranged on the receiving surface of a device for improving the sperm quality according to an embodiment of the invention. In 901 first information regarding health is inputted, in 902 second information regarding lifestyle is inputted, in 903 lifestyle recommendations are derived, in 904 the lifestyle recommendations are returned.

Figure 10:
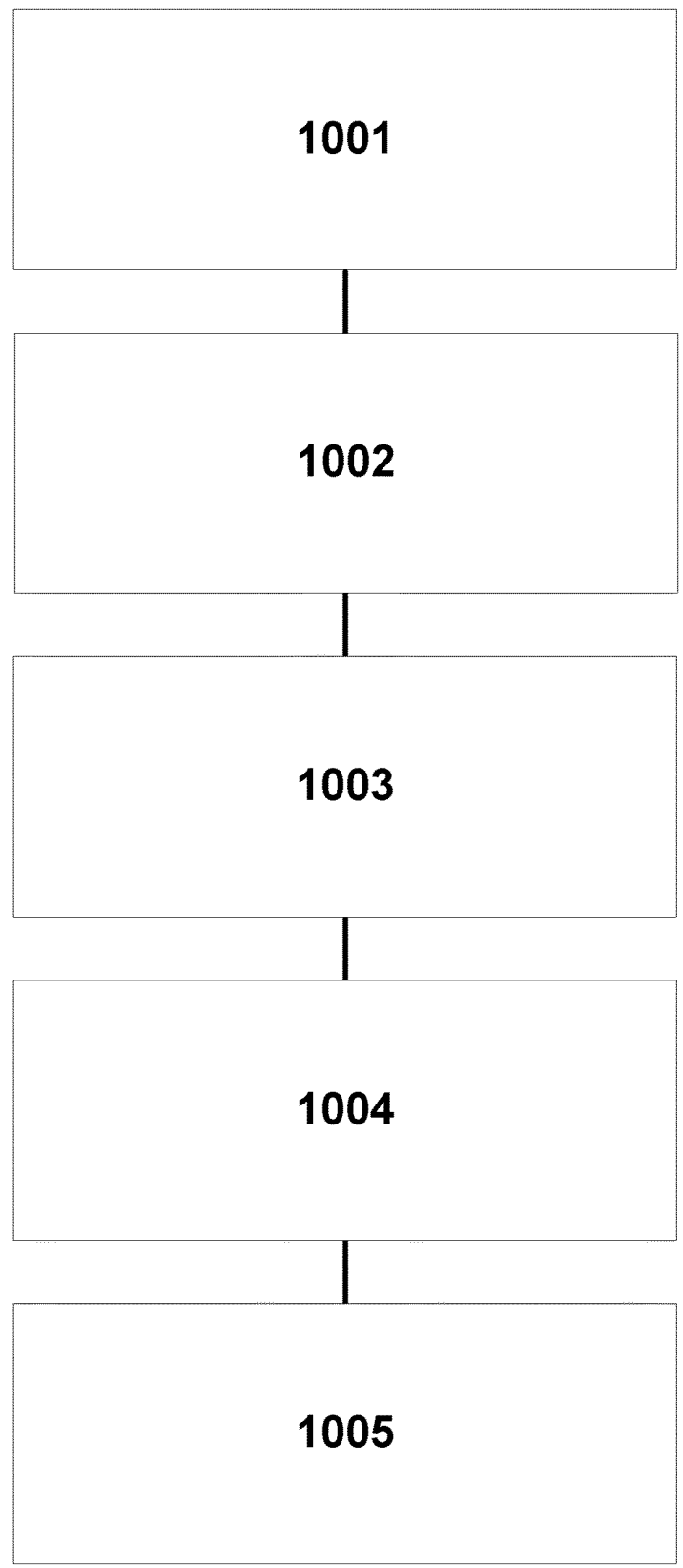
FIG. 10 shows an example of use of an electronic apparatus, arranged on the receiving surface of a device for improving the sperm quality according to an embodiment of the invention.

FIG. 10 shows an embodiment of the use of an electronic apparatus, arranged on the receiving surface of a device for improving the sperm quality according to an embodiment of the invention. In 1001 first information regarding health is inputted, in 1002 second information regarding lifestyle is inputted, in 1003 third information regarding sperm quality is inputted, in 1004 lifestyle recommendations are derived, in 1005 the lifestyle recommendations are returned.

Table 1 shows an embodiment of labelling the measured sperm concentration (C), where a sperm concentration higher than 50M/ml is labelled very high, a sperm concentration between 40-50M/ml is labelled high, a sperm concentration between 20-40M/ml is labelled moderate, a sperm concentration between 5-20M/ml is labelled low, and a sperm concentration between 0-5M/ml labels the sample for additional analysis. Furthermore, the embodiment also illustrates a labelling of the measured motility (M), where a motility between 40-100% is labelled as very high, a motility between 30-40% is labelled as high, a motility between 20-30% is labelled as moderate, a motility between 0-20% is labelled as low. The table and the ranges of the concentrations and motility are suggestions, and may be different in different embodiments.

Table 1 shows an embodiment of the analysis based on concentration and motility

|  |  | Motility (M) | | |
|---|---|---|---|---|
|  |  | 0-32% | 32-40% | 40-100% |
| Sperm Conc (C) | 0-5 M/ml | We are sorry but we could not detect any sperm cells. Please try again to make sure it was not an error with the device. If this was your second attempt, press "Send video to expert" to get one of our experts to take a look. | | |
|  | 5-15 M/ml | We could detect C million cells/ml, which is a low concentration of sperm cells. M % of them moved which is very low. Because of a low concentration and low motility, we suggest that you follow our intervention program to increase your chances of pregnancy with your partner. | We could detect C million cells/ml, which is a low concentration of sperm cells. M % of them moved which is moderate. Because of a low concentration and a moderate motility, we suggest that you follow our intervention program to increase your chances of pregnancy with your partner. | We could detect C million cells/ml, which is a low concentration of sperm cells. M % of them moved which is high. Because of a low concentration, we suggest that you follow our intervention program to increase your chances of pregnancy with your partner. |
|  | 15-55 M/ml | We could detect C million cells/ml, which is a moderate concentration of sperm cells. M % of them moved which is very low. We suggest that you follow our intervention program because increasing both concentration and motility will increase the chances of pregnancy with your partner. | We could detect C million cells/ml, which is a moderate concentration of sperm cells. M % of them moved which is moderate. We suggest that you follow our intervention program because increasing both concentration and motility will increase the chances of pregnancy with your partner. | We could detect C million cells/ml, which is a moderate concentration of sperm cells. M % of them moved which is high. We suggest that you follow our intervention program because increasing your concentration will increase the chances of pregnancy with your partner. |
|  | 55-above M/ml | We could detect C million cells/ml, which is a high concentration of sperm cells. M % of them moved which is very low. We suggest that you follow our intervention program because increasing the motility of your sperm cells will increase the chances of pregnancy with your partner. | We could detect C million cells/ml, which is a high concentration of sperm cells. M % of them moved which is moderate. Your sperm quality is high, but we suggest that you follow our intervention program because increasing the motility of your sperm cells will increase the chances of pregnancy with your partner. | We could detect C million cells/ml, which is a high concentration of sperm cells. M % of them moved which is high. Your sperm quality is high, but we suggest that you follow our intervention program to potentially improve other sperm parameters. |

Although some embodiments have been described and shown in detail, the invention is not restricted to them, but may also be embodied in other way within the scope of the subject matter defined in the following claims. In particular, it is understood that other embodiments may be utilised and structural and functional modifications may be made without departing from the scope of the present invention.

The invention claimed is:

1. A device for testing the quality of a biological sample in cooperation with an electronic apparatus, wherein the device comprises;
   a slide slot adapted for receiving a slide containing a biological sample;
   a receiving surface adapted for receiving an electronic apparatus containing a camera, where the receiving surface comprises a through hole extending through said receiving surface, so that when the electronic apparatus is placed on said receiving surface, the through hole is arranged adjacent to the camera of the electronic apparatus;
   a light source arranged opposite the through hole, and adapted to emit light that illuminates and at least partly propagates through the sample and said through hole, so that a camera, when placed at the through hole, receives at least part of the emitted light;
   a lens arranged between the slide slot and the receiving surface, and adapted to magnify the image received at the receiving surface;
   wherein the slide slot is arranged between the light source and the through hole, the device further comprising a housing attached opposite the receiving surface, the housing having a shape allowing for a plurality of stable resting conditions in which the electronic apparatus lies on the receiving surface, wherein alignment between the camera and the through hole is maintained by rotation of the device and alignment between the camera and the through hole is further maintained by friction, and
   wherein the housing having an outer side with at least two faces, the two faces are arranged at an angle to each other, wherein the device is stable, when the device is arranged on either face, so that alignment of the through hole with a camera of an electronic apparatus is retained, when an electronic apparatus is placed on the receiving surface.

2. The device according to claim 1, wherein the shape of the housing is rounded.

3. The device according to claim 1, wherein the outer side of the housing has a coefficient of friction larger than 0.3.

4. The device according to claim 1, wherein the receiving surface and the housing are separate elements.

5. The device according to claim 1, wherein the lens is arranged in the through hole.

6. The device according to claim 1, wherein the slide slot extends partially along the receiving surface.

7. A method for testing the quality of a biological sample comprising the steps of:
   placing an electronic apparatus on the receiving surface of a device according to claim 1, such that the camera of the electronic apparatus is arranged adjacent to the through hole of the device;
   recording a video of the biological sample with the camera of the electronic apparatus;
   identifying a plurality of biological cells in the biological sample based on the recorded video;
   determining a location of a first biological cell of the plurality of biological cells in a first frame of the recorded video;
   identifying the first biological cell in a second frame of the recorded video;
   determining a location of the first biological cell in the second frame;
   returning the detected motility and/or concentration of the plurality of biological cells in the biological sample.

8. The method according to claim 7, wherein the method further comprises the step of uploading the video and/or the motility, concentration of the biological sample, or any combination thereof.

9. The method according to claim 7, wherein the method further comprises the step of providing a digital label to the detected cell concentration.

10. A method of improving sperm quality comprising the steps of: employing an electronic apparatus, arranged on the receiving surface of a device according to claim 1;
    inputting first information regarding physical health into the electronic apparatus;
    inputting second information regarding lifestyle into the electronic apparatus;
    deriving lifestyle recommendations for improving the sperm quality based on the first and second information;
    returning the lifestyle recommendations.

11. The method of claim 10, wherein the method further comprises the step of:
    inputting third information regarding the current sperm quality into the electronic apparatus, the third information comprises at least the sperm concentration and motility;
    deriving lifestyle recommendations for improving the sperm quality based on the first, second and third information.

12. The method of claim 11, wherein the third information is obtained through a method comprising the steps of:
    placing the electronic apparatus on the receiving surface of the device according to claim 1, such that the camera of the electronic apparatus is arranged adjacent to the through hole of the device;
    recording a video of the biological sample with the camera of the electronic apparatus;
    identifying a plurality of biological cells in the biological sample based on the recorded video;
    determining a location of a first biological cell of the plurality of biological cells in a first frame of the recorded video;
    identifying the first biological cell in a second frame of the recorded video;
    determining a location of the first biological cell in the second frame;
    returning the detected motility and/or concentration of the plurality of biological cells in the biological sample.

13. The device according to claim 1, wherein the shape of the housing is semi-circular.

14. The device of claim 1, wherein the biological sample is semen.

15. The method of claim 7, wherein the biological sample is semen.

* * * * *